US010022048B2

(12) United States Patent
Pujol Ramo et al.

(10) Patent No.: US 10,022,048 B2
(45) Date of Patent: Jul. 17, 2018

(54) METHOD, SYSTEM AND COMPUTER PROGRAM FOR MEASURING LIGHT DIFFUSION IN THE EYEBALL OR IN THE OCULAR REGION

(71) Applicant: UNIVERSITAT POLITÈCNICA DE CATALUNYA, Barcelona (ES)

(72) Inventors: Jaume Pujol Ramo, Barcelona (ES); Montserrat Arjona Carbonell, Barcelona (ES); Carlos Enrique Garcia Guerra, Barcelona (ES); Mikel Aldaba Arévalo, Barcelona (ES); Meritxell Vilaseca Ricart, Barcelona (ES); Fernando Díaz Doutón, Barcelona (ES)

(73) Assignee: UNIVERSITAT POLITECNICA DE CATALUNYA, Barcelona (ES)

(*) Notice: Subject to any disclaimer, the term of this patent is extended or adjusted under 35 U.S.C. 154(b) by 0 days.

(21) Appl. No.: 15/500,208

(22) PCT Filed: Jul. 29, 2015

(86) PCT No.: PCT/ES2015/070586
§ 371 (c)(1),
(2) Date: Jan. 30, 2017

(87) PCT Pub. No.: WO2016/016499
PCT Pub. Date: Feb. 4, 2016

(65) Prior Publication Data
US 2017/0258324 A1 Sep. 14, 2017

(30) Foreign Application Priority Data

Jul. 31, 2014 (ES) .................................. 201431163

(51) Int. Cl.
*A61B 3/14* (2006.01)
*A61B 3/00* (2006.01)
(Continued)

(52) U.S. Cl.
CPC .............. *A61B 3/1035* (2013.01); *A61B 3/12* (2013.01); *A61B 3/145* (2013.01); *A61B 3/18* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| 2005/0057723 | A1* | 3/2005 | Wakil | A61B 3/022 |
| | | | | 351/246 |
| 2007/0070292 | A1* | 3/2007 | Liang | A61B 3/156 |
| | | | | 351/205 |
| 2010/0195876 | A1* | 8/2010 | Artal Soriano | A61B 3/101 |
| | | | | 382/128 |

FOREIGN PATENT DOCUMENTS

| EP | 2147633 | 1/2010 |
| ES | 2265225 | 2/2007 |

(Continued)

OTHER PUBLICATIONS

International Search Report of PCT/ES2015/070586 dated Oct. 8, 2015.
(Continued)

*Primary Examiner* — Mohammed Hasan

(57) ABSTRACT

Method, system and computer program for measuring light diffusion in the eyeball or in the ocular region.
The method comprises:
  projecting a punctiform light beam onto the retina;
  correcting low-order ocular aberrations of the eye;
(Continued)

capturing and recording an image of the retinal plane formed after reflection of the punctiform light beam on the retina and a double passage through the ocular media of the eye; and at the same time as capturing the image of the retinal plane, performing a high- and low-order ocular aberration measurement in the plane of the pupil and performing a light diffusion measurement, combining ocular aberration measurement information with information on the image of the retinal plane.

The system and the computer program are adapted for implementing the method.

19 Claims, 1 Drawing Sheet

(51) Int. Cl.
*A61B 3/103* (2006.01)
*A61B 3/12* (2006.01)
*A61B 3/18* (2006.01)

(58) Field of Classification Search
USPC .................................. 351/200–246
See application file for complete search history.

(56) References Cited

FOREIGN PATENT DOCUMENTS

| ES | 2315171 | 3/2009 |
|---|---|---|
| WO | 2007035334 | 3/2007 |

OTHER PUBLICATIONS

Fernando Diaz Douton et al. "Comparison of the Retinal Image Quality with a Hartmann-Shack Wavefront Sensor and a Double-Pass Instrument", Investigative Ophthalmology & Visual Science, Apr. 2006, vol. 47, No. 4.

Gerald Westheimer et al. "Evaluating Diffusion of Light in the Eye by Objective Means" Investigative Ophthalmology & Visual Science, Apr. 1994, vol. 35, No. 5.

Guell et al. "Optical Quality Analysis System: Instrument for objective clinical evaluation of ocular optical quality", J Cataract Refract Surg—vol. 30, Jul. 2004.

Santamaria et al. "Determination of the point-spread function of human eyes using a hybrid optical-digital method" vol. 4, No. 6/Jun. 1987/J. Opt. Soc. Am. A.

\* cited by examiner

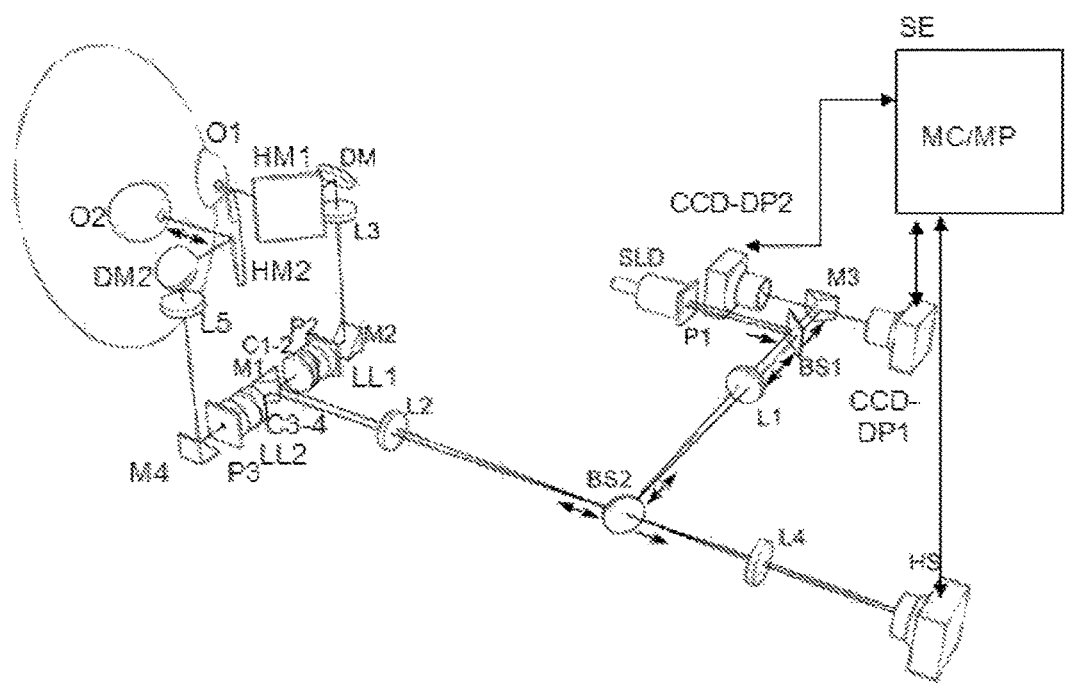

METHOD, SYSTEM AND COMPUTER PROGRAM FOR MEASURING LIGHT DIFFUSION IN THE EYEBALL OR IN THE OCULAR REGION

RELATED APPLICATIONS

This application is the US national phase application of international application number PCT/ES2015/070586, filed 29 Jul. 2015, which designates the US and which claims priority to Spanish application ES P201431163 filed 31 Jul. 2014, the contents of each of which are hereby incorporated by reference as if set forth in their entireties.

TECHNICAL FIELD

The present invention generally relates, in a first aspect, to a method for measuring light diffusion in the eyeball or in the ocular region, and more particularly to a method combining ocular aberration measurements information with information on the image of the retinal plane of one or both eyes of a patient.

A second aspect of the invention relates to a system suitable for implementing the method of the first aspect.

A third aspect of the invention relates to a computer program suitable for implementing the method of the first aspect.

PRIOR ART

Light diffusion in the eyeball or in the ocular region is one of the three causes of image quality deterioration in the retina in the human eye, the other two causes being optical aberrations and diffraction.

The combined contribution of optical aberrations and intraocular diffusion affects retinal image quality. The double-pass technique (J. Santamaria, P. Artal, J. Bescos, "Determination of the point-spread function of human eyes using a hybrid optical-digital method", J., Opt. Soc. Am. A, 4, 1109-1114 (1987)), based on projecting a collimated light beam onto the retina of a patient, and directly recording the light reflected therein after the double passage of the light through the ocular media, allows obtaining an objective measurement of the contribution of aberrations and intraocular diffusion to ocular optical quality (F. Diaz-Douton, A. Benito, J. Pujol, M. Arjona, J L Güell P. Artal, "Comparison of the retinal image quality obtained with a Hartmann-Shack sensor and a double-pass instrument", Inv. Ophthal. Vis. Ciencia., 47, 1710-1716 (2006)).

In the article entitled "Comparison of the retinal image quality obtained with a Hartmann-Shack sensor and a double-pass instrument", F. Diaz-Douton, A. Benito, J. Pujol, M. Arjona, J L Güell, P. Artal, Inv. Ophthal. Vis. Ciencia., 47, 1710-1716 (2006), describes the separate use of both the double-pass technique and of the ocular aberrations measurement technique by means of sensors of wavefront (particularly by means of a Hartmann-Shack sensor), for the purpose of comparing the results obtained by means of both techniques for determining when one is better than the other when estimating the quality of the image of the retina, concluding that for eyes with low intraocular diffusion, both techniques offer similar results, and that, in contrast, for eyes with intermediate or high intraocular diffusion values the double-pass technique is better because it produces a more precise description of the optical quality, best correlated with vision quality, whereas the aberration measurement technique can produce results that overestimate the retinal image quality.

At no point does said article propose combining the results obtained by means of using each of the two mentioned techniques for obtaining a combined result, or measuring light diffusion in the eyeball or in the ocular region, or performing any other kind of measurement.

In addition, patent application EP2147633A1 proposes a method and a system for measuring light diffusion in the eyeball or in the ocular region, which comprises performing the steps described in the preamble of claim 1 of the present invention.

DESCRIPTION OF THE INVENTION

It is necessary to offer an alternative to the prior art that covers the voids therein, by providing a light diffusion measurement in the eyeball or in the ocular region that is more precise than the one obtained by means of the proposals from the prior art.

For that purpose, the present invention relates, in a first aspect, to a method for measuring light diffusion in the eyeball or in the ocular region, which comprises performing the following steps:

projecting a punctiform light beam onto the retina of at least one eye of a patient;
correcting low-order ocular aberrations of said eye; and
capturing and recording, once said low-order aberrations have been corrected, at least one image of the retinal plane formed after reflection of said punctiform light beam on the retina and a double passage through the ocular media of said eye.

Unlike the known methods for taking measurement, where at most one ocular aberration measurement has been used to validate the results obtained by means of processing an image of the retinal plane and the information on said image, the method proposed by the first aspect of the invention characteristically comprises, at the same time as said capturing of said image of the retinal plane, taking a high- and low-order ocular aberration measurement in the plane of the pupil of said eye and taking a light diffusion measurement, combining information obtained by means of said ocular aberration measurement with information on said image of the retinal plane.

Capturing the image of the retinal plane and taking the high- and low-order ocular aberration measurement at the same time is essential for obtaining good results as regards the light diffusion measurement, because if they did not take place at the same time, the conditions in which both measurements (the measurement associated with capturing the image of the retinal plane and the ocular aberration measurement) would be taken would not be identical or similar enough to be combined with one another.

Said low-order aberrations preferably include astigmatism and defocusing.

According to one embodiment, the method proposed by the first aspect of the invention is implemented using open field techniques and/or in a binocular manner in both eyes of the patient.

According to one embodiment, the high- and low-order ocular aberration measurement is a second measurement, wherein the method comprises previously taking a first ocular aberration measurement of the eye of the patient and using the obtained results for the mentioned correcting of low-order ocular aberrations of said eye.

Low-order ocular aberrations can be corrected using any technique known, ranging from the technique associated with a standard methodology to the technique disclosed by the authors of the present invention in patent application EP2147633A1.

Advantageously, the method of the first aspect of the invention comprises using one and the same system for measuring aberrations (generally an aberrometer) for taking the first and second ocular aberration measurements. For another less preferred embodiment, are used two systems for measuring aberrations, one for each of the first and second measurements.

The method comprises performing the mentioned high- and low-order ocular aberration measurement on the wavefront coming from the reflection of said punctiform light beam on the retina, as it passes through the plane of the pupil.

According to one embodiment, the method of the present invention comprises analyzing the distribution of light of the image of the retinal plane and the of an image corresponding to said ocular aberration measurement on said wavefront, in the plane of the pupil, and taking a light diffusion measurement by comparing both distributions of light, advantageously for each of the light spots of both images.

For one embodiment, the method comprises calculating the objective scatter index (OSI) described in patent application EP2147633A1 with the information on the image of the retinal plane, and combining the result obtained with the result obtained by applying any known methodology to the ocular aberration measurement information, for obtaining the final light diffusion measurement.

For another embodiment, the method comprises applying respective optical transfer functions, or OTF, to the ocular aberration measurement information and to the information on the image of the retinal plane and taking a light diffusion measurement, combining the results provided by said OTF functions.

According to a variant of said embodiment, the method proposed by the first aspect of the invention comprises performing the light diffusion measurement, combining the results provided by said OTF functions and also comparing both of said distributions of light.

As regards OTF functions, said functions include at least absolute values in respective modulation transfer functions, or MTF, wherein the method comprises performing the light diffusion measurement dividing values associated with profiles (for example radial profiles or one-way profiles) generated with said absolute values, for example calculating the existing areas under the curves of said profiles, performing said division with the values calculated for said areas.

According to one embodiment, said OTF functions include complex argument values in respective phase transfer functions, or PTF.

A second aspect of the present invention relates to a system for measuring light diffusion in the eyeball or in the ocular region, comprising:

means for projecting a punctiform light beam onto the retina of at least one eye of a patient;

means for capturing and recording an image of the retinal plane formed after reflection of said punctiform light beam on the retina and a double passage through the ocular media of said eye; and means for correcting low-order ocular aberrations of said eye prior to said capturing and recording.

Unlike known systems, the system proposed by the second aspect of the present invention comprises means for taking a high- and low-order ocular aberration measurement in the plane of the pupil of said eye;

control means controlling at least said means for capturing and recording an image of the retinal plane and said means for taking an ocular aberration measurement, so that they operate at the same time; and processing means processing, in a combined manner, information obtained by means of said ocular aberration measurement with information on said image of the retinal plane and providing, as a result of said processing, the value or values of said light diffusion measurement.

The system proposed by the second aspect of the invention is provided for implementing the method according to the first aspect.

Preferably, the mentioned means for projecting a punctiform light beam onto the retina of an eye of a patient and the means for capturing and recording an image of the retinal plane are part of a double-pass ophthalmoscopic system.

Advantageously, the system proposed by the second aspect of the invention is configured and arranged for using open field techniques.

For a preferred embodiment, the system proposed by the second aspect of the invention is configured and arranged for implementing a binocular system applied to both eyes of the patient.

For another less preferred embodiment, the system proposed by the second aspect of the invention is configured and arranged for implementing a monocular system.

According to a preferred embodiment, the means for correcting low-order ocular aberrations comprise or are associated with the means for taking an ocular aberration measurement, for correcting ocular aberrations depending on measurements taken with the means for taking an ocular aberration measurement.

For another less preferred embodiment, the means for correcting low-order ocular aberrations and the means for taking an ocular aberration measurement are independent from one another.

A third aspect of the present invention relates to a computer program including code instructions which, when run in a computer, take a light diffusion measurement in the eyeball or in the ocular region according to the method of the first aspect, processing, in a combined manner, data corresponding to the information obtained by means of the ocular aberration measurement with data corresponding to the information on the image of the retinal plane.

BRIEF DESCRIPTION OF THE DRAWINGS

The foregoing and other advantages and features will be better understood based on the following detailed description of several embodiments making reference to the attached drawings, which must be interpreted in a non-limiting illustrative manner, in which:

FIG. 1 is a perspective view of a schematic depiction of the system proposed by the second aspect of the present invention for an embodiment in which an open field binocular system is implemented.

DETAILED DESCRIPTION OF SEVERAL EMBODIMENTS

According to the embodiment illustrated in FIG. 1, the system for measuring light diffusion in the eyeball or in the ocular region proposed by the second aspect of the present invention is an open field binocular system comprising means for projecting a punctiform light beam onto the retina of both eyes O1, O2 of a patient, which include a punctiform light source SLD generating a collimated (generally a laser light) beam which is distributed into two respective emission sub-beams by a mask or pupil P1, which are directed towards each of the two eyes O1, O2 by a series of common optical elements, particularly beam splitters BS1 and BS2 acting as mirrors and lenses L1 and L2, and after each of the emission sub-beams is redirected towards the respective eye O1, O2 by the mirror M1, each of them is individually directed by one of respective groups of optical elements, each of them formed particularly by a pair of cylindrical lenses C1-2 and C3-4, after which there are arranged another lens LL1 and LL2, another pupil P2 and P3, a respective mirror M2 and M4, another lens L3 and L5, a dichroic mirror DM1 and DM2 and, finally, a heat mirror HM1 and HM2, after which the emission sub-beam strikes the retina of the eye O1, O2.

FIG. 1 also shows how the system comprises means consisting of two cameras CCD-DP1y CCD-DP2, each of them provided for capturing and recording an image of the plane of one of the retinas, which image is formed after reflection of the two punctiform light emission sub-beams in the retina and a double passage through the ocular media of both eyes O1, O2, generating respective reflection sub-beams following a path opposite the emission sub-beam path, going through the optical elements to the beam splitter BS2, which reflects a portion of each of the reflection sub-beams, going through the lens L1 and the beam splitter BS1, after which each of the reflection sub-beams is directed to one of the cameras CCD-DP1 and CCD-DP2 by the mirror M3.

The pairs of cylindrical lenses C1-2 and C3-4 are part of or are means for correcting low-order ocular aberrations of the eyes O1, O2 prior to capturing and recording the images of the retinal planes.

In addition, FIG. 1 also shows how the system also comprises means for performing a high- and low-order ocular aberration measurement in the plane of the pupil of both eyes O1, O2, which particularly consists of a Hartmann-Shack sensor HS, which is struck by portions of the two reflection sub-beams going through the beam splitter BS2 and the lens L4.

FIG. 1 likewise illustrates, by means of arrows, the direction of the light in the first and second passage, i.e., the emission sub-beams towards the retinas and the reflection sub-beams in the opposite direction.

FIG. 1 also illustrates an electronic system SE communicated in a bidirectional manner with the cameras CCD-DP1, CCD-DP2 and the Hartmann-Shack sensor HS, and comprising control means MC controlling at least CCD-DP1, CCD-DP2 and HS so that they operate at the same time, and processing means MP processing, in a combined manner, information obtained by means of CCD-DP1, CCD-DP2 and HS and providing, as a result of said processing, the value or values of the light diffusion measurement.

For a non-illustrated embodiment, the control means MC are connected with the pairs of cylindrical lenses C1-2 and C3-4 (and/or with any other type of alternative mechanism suitable for correcting low-order ocular aberrations) to control them for the purpose of the mentioned correcting of ocular aberrations, depending on ocular aberration measurements taken with the Hartmann-Shack sensor HS.

A person skilled in the art could introduce changes and modifications in the described embodiments without departing from the scope of the invention as it is defined in the attached claims.

The invention claimed is:

1. A method for measuring light diffusion in the eyeball or in the ocular region, which comprises performing the following steps:
   projecting a punctiform light beam onto the retina of at least one eye of a patient;
   performing a first ocular aberrations measurement of said at least one eye of the patient and using the obtained results for correcting low-order ocular aberrations of said eye; and
   capturing and recording, once said low-order aberrations have been corrected, at least one image of a retinal plane formed after reflection of said punctiform light beam on the retina and a double passage through the ocular media of said eye;
   wherein the method comprises, at the same time as said capturing and recording performing a second high- and low-order ocular aberration measurement in a plane of the pupil of said eye, and further performing a light diffusion measurement, combining information obtained by means of said second high- and low-order ocular aberrations measurement with information of said image of the retinal plane.

2. The method according to claim 1, wherein it is implemented using open field techniques.

3. The method according to claim 1, wherein it is implemented in a binocular manner in both eyes of the patient.

4. The method according to claim 1, wherein it comprises performing said high- and low-order ocular aberration measurement on a wavefront coming from the reflection of said punctiform light beam on the retina, as it passes through the plane of the pupil.

5. The method according to claim 4, wherein it comprises analyzing the distribution of light of the image of the retinal plane and the distribution of light of an image corresponding to said ocular aberration measurement on said wavefront, in the plane of the pupil, and performing a light diffusion measurement by comparing both distributions of light.

6. The method according to claim 5, wherein it comprises analyzing said distribution of light for each of the light spots of both images.

7. The method according to claim 5, wherein it comprises applying respective optical transfer functions, termed OTF, to the ocular aberration measurement information and to the information on the image of the retinal plane, and performing a light diffusion measurement, combining the results provided by said OTF functions.

8. The method according to claim 7, wherein it comprises performing the light diffusion measurement, combining the results provided by said OTF functions and also by comparing both of said distributions of light.

9. The method according to claim 8, wherein said OTF functions include at least absolute values in respective modulation transfer functions, termed MTF, wherein the method comprises performing the light diffusion measurement, dividing values associated with profiles generated with said absolute values.

10. The method according to claim 9, wherein it comprises obtaining said values associated with said profiles, calculating the existing areas under the curves of said profiles, performing said division with the values calculated for said areas.

11. The method according to claim 8, wherein said OTF functions include complex argument values in respective phase transfer functions, or PTF.

12. The method according to claim 1, wherein it comprises using one and the same system for measuring aberrations for performing said first and second ocular aberration measurements.

13. The method according to claim 1, wherein said low-order aberrations include astigmatism and defocusing.

14. A system for measuring light diffusion in the eyeball or in the ocular region, comprising:
   a light source configured to project a punctiform light beam onto the retina of at least one eye of a patient;
   at least one camera configured to capture and record an image of a retinal plane formed after reflection of said punctiform light beam on the retina and a double passage through the ocular media of said at least one eye; and
   at least a pair of cylindrical lenses configured to correct low-order ocular aberrations of said at least one eye prior to said capturing and recording;
   wherein the system further comprises:
   an aberrometer configured to perform a first ocular aberrations measurement of the at least one eye of the patient, wherein a result of the first ocular measurement is used for performing said correction of the low-order aberrations, and configured to perform a second high- and low-order ocular aberrations measurement in a plane of the pupil of said eye;
   a control unit configured to control at least said camera and said aberrometer for performing said second ocular aberrations measurement, so that they operate at the same time; and
   a processing unit configured to process, in a combined manner, information obtained by the at least one camera with information obtained by the aberrometer and providing, as a result of said processing, the value or values of said light diffusion measurement.

15. The system according to claim 14, wherein said light source and said at least one camera are part of a double-pass ophthalmoscopic system.

16. The system according to claim 14, wherein it is configured and arranged for using open field techniques.

17. The system according to claim 14, wherein it is configured and arranged for implementing a binocular system applied to both eyes of the patient.

18. The system according to claim 14, wherein said pair of cylindrical lenses comprise or are associated with said aberrometer, for performing said correcting of ocular aberrations depending on measurements taken with the aberrometer.

19. A non-transitory computer readable storage medium including code instructions which, when run in a computer, measure light diffusion in the eyeball or in the ocular region according to a method comprising:
   projecting a punctiform light beam onto the retina of at least one eye of a patient;
   performing a first ocular aberrations measurement of said at least one eye of the patient and using the obtained results for correcting low-order ocular aberrations of said eye; and
   capturing and recording, once said low-order aberrations have been corrected, at least one image of a retinal plane formed after reflection of said punctiform light beam on the retina and a double passage through the ocular media of said eye;
   wherein the method comprises, at the same time as said capturing and recording, performing a second high- and low-order ocular aberration measurement in the plane of the pupil of said eye, and further performing a light diffusion measurement, combining information obtained by means of said second high- and low-order ocular aberrations measurement with information of said image of the retinal plane, and
   processing, in a combined manner, data corresponding to the information obtained by means of measuring ocular aberrations with data corresponding to the information on the image of the retinal plane.

* * * * *